US006797400B2

(12) United States Patent
Weuthen et al.

(10) Patent No.: US 6,797,400 B2
(45) Date of Patent: Sep. 28, 2004

(54) MOIST WIPES (II)

(75) Inventors: Manfred Weuthen, Langenfeld (DE); Michael Elsner, Solingen (DE); Anja Hanke, Duisburg (DE)

(73) Assignee: Cognis Deutschland GmbH & Co. KG, Duesseldorf (DE)

( * ) Notice: Subject to any disclaimer, the term of this patent is extended or adjusted under 35 U.S.C. 154(b) by 0 days.

(21) Appl. No.: 10/240,976

(22) PCT Filed: Mar. 30, 2001

(86) PCT No.: PCT/EP01/03631

§ 371 (c)(1),
(2), (4) Date: Oct. 7, 2002

(87) PCT Pub. No.: WO01/76445

PCT Pub. Date: Oct. 18, 2001

(65) Prior Publication Data

US 2003/0124373 A1 Jul. 3, 2003

(30) Foreign Application Priority Data

Apr. 7, 2000 (DE) .......................... 100 17 189

(51) Int. Cl.⁷ .......................... B32B 23/04; B32B 29/00
(52) U.S. Cl. .................. 428/532; 428/535; 428/536; 428/537.5; 424/402; 424/400; 424/443; 424/449
(58) Field of Search ................. 428/532, 535, 428/536, 537.5; 424/400, 402, 443, 449

(56) References Cited

U.S. PATENT DOCUMENTS

| 3,896,807 A | 7/1975 | Buchalter |
| 3,956,155 A | 5/1976 | Schwuger |
| 4,189,395 A | 2/1980 | Bland |
| 4,666,621 A | 5/1987 | Clark et al. |
| 5,094,770 A | 3/1992 | Sheridan et al. |
| 5,374,716 A | 12/1994 | Biermann et al. |
| 5,576,425 A | 11/1996 | Hill et al. |
| 5,817,585 A | 10/1998 | Rose et al. |
| 6,146,648 A | 11/2000 | Bret et al. |
| 6,623,746 B1 * | 9/2003 | Wadle et al. ............... 424/402 |

FOREIGN PATENT DOCUMENTS

| DE | 1 165 574 | 8/1960 |
| DE | 2 024 051 | 5/1970 |
| DE | 197 56 377 | 6/1999 |
| EP | 0 301 298 | 2/1989 |
| WO | WO 90/03977 | 4/1990 |
| WO | WO 95/35411 | 12/1995 |
| WO | WO 97/30217 | 8/1997 |

OTHER PUBLICATIONS

J. Falbe, "Surfactants in Consumer Products", pp.54–125, Springer Verlag, Berlin, 1987.

J. Falbe et al., "Katalysatoren, Tenside und Mineraloladditive" Catalysts, Surfactants and Mineral Oil Additives pp. 123–217, Thieme Verlag.Stuttgart, 1987.

* cited by examiner

*Primary Examiner*—Leszek Kiliman
(74) *Attorney, Agent, or Firm*—Aaron R. Ettelman; Steven J. Trzaska

(57) ABSTRACT

A cleansing article having a substrate capable of absorbing and retaining a fluid therein, the substrate being impregnated with a cleaning composition containing a linear and/or branched alcohol polyglycol ether.

13 Claims, No Drawings

MOIST WIPES (II)

This application is a 371 of PCT/EP01/03631 filed Mar. 30, 2001.

BACK GROUND OF THE INVENTION

The invention is in the field of cleaners for hard surfaces and relates to wet wipes which are impregnated with a special species of a nonionic surfactant.

For the cleaning of hard surfaces, liquids of greater or lesser viscosity are usually used, which are applied directly, run off from the surface to be cleaned and in so doing carry along the majority of the soiling. Another application form which is enjoying increased importance are wet wipes, which are textile fabrics or else tissue papers which are impregnated with a cleaning liquid. Thus, for example, international patent application WO 95/35411 (Procter & Gamble) proposes wet wipes albeit predominantly for cosmetic applications, which comprise, in addition to mineral oil, fatty acid esters, fatty alcohol ethoxylates and fatty alcohols.

The disadvantage of the use of these wet wipes is that the surfactants used leave behind a residue in the form of smearing, which makes the treated surface less shiny or even makes it appear soiled. A further problem arises in the production of the wet wipes. In order to impregnate the fabric or tissue paper with the cleaning solution, it is either sprayed therewith or immersed therein where, in both cases, it is possible for the output in production to be reduced as a result of foam formation or insufficient wetting. A first object of the present invention was therefore to provide wet wipes using special surfactants which are free from the problems described above.

For logistical reasons, the use of concentrates for the preparation of impregnation solutions for the wet wipes is advantageous. It is disadvantageous that the concentrates often show a tendency toward foam formation upon dilution. Furthermore, gel phases may form, which leads to increased time expenditure in the preparation of the impregnation solutions. In both cases, the production output is reduced. A further object of the invention was therefore to provide surfactants with which concentrates can be prepared which, by virtue of their viscosity, storage stability, lack of foam upon dilution and rapid dilutability, permits a technically simple and therefore cost-effective production of the wet wipes.

DESCRIPTION OF THE INVENTION

The invention provides wet wipes which are characterized in that they are impregnated with linear and/or branched alcohol polyglycol ethers.

Surprisingly, it has been found that nonionic surfactants of the linear and/or branched alcohol polyglycol ether type, preferably in combination with alkyl oligoglucosides, satisfy the complex object in an excellent manner. Impregnating agents based on alcohol polyglycol ethers have proven in the application to be low-viscosity and virtually foam-free, and in application the wet wipes impregnated therewith do not leave behind any streaks and do not impair the shine. Concentrates based on alcohol polyglycol ethers are low-viscosity and, upon dilution to the application concentration, particularly low-foaming.

Alcohol Polyglycol Ethers

Alcohol polyglycol ethers are known nonionic surfactants which are usually obtained by adding ethylene oxide and/or propylene oxide, blockwise or in random distribution, onto suitable primary alcohols or polyols. The polyglycol ethers usually conform to the formula (I),

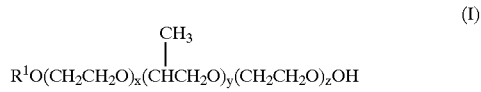

$$R^1O(CH_2CH_2O)_x(\overset{\overset{\displaystyle CH_3}{|}}{C}HCH_2O)_y(CH_2CH_2O)_zOH \qquad (I)$$

in which $R^1$ is a linear and/or branched alkyl and/or alkenyl radical having 6 to 22, preferably 8 to 18 and in particular 10 to 12, carbon atoms, an ethylene glycol or glycerol radical, x and z, independently of one another, are 0 or numbers from 1 to 40 and y is numbers from 1 to 40; the polyglycol ethers thus obligatorily contain at least one propylene oxide unit. Typical examples are the addition products of, on average, 1 to 40, preferably 5 to 30 and in particular 8 to 15, mol of ethylene oxide and/or 1 to 10, preferably 2 to 5, mol of propylene oxide onto fatty alcohols, oxo alcohols or alfols, such as, for example, caproic alcohol, caprylic alcohol, 2-ethylhexyl alcohol, capric alcohol, lauryl alcohol, isotridecyl alcohol, myristyl alcohol, cetyl alcohol, palmoleyl alcohol, stearyl alcohol, isostearyl alcohol, oleyl alcohol, elaidyl alcohol, petroselinyl alcohol, linolyl alcohol, linolenyl alcohol, elaeostearyl alcohol, arachyl alcohol, gadoleyl alcohol, behenyl alcohol, erucyl alcohol and brassidyl alcohol, and technical-grade mixtures thereof, and also ethylene glycol or glycerol. The amount of alcohol polyglycol ethers used can, based on the wet wipes, be 0.05 to 2% by weight and preferably 0.1 to 0.5% by weight and, based on the concentrates, 10 to 50% by weight, preferably 15 to 25% by weight.

Cosurfactants

In a preferred embodiment of the present invention, the mixed ethers are used together with further anionic, nonionic, cationic and/or amphoteric or zwitterionic surfactants.

Typical examples of anionic surfactants are soaps, alkylbenzenesulfonates, alkanesulfonates, olefin-sulfonates, alkyl ether sulfonates, glycerol ether sulfonates, α-methyl ester sulfonates, sulfo fatty acids, alkyl sulfates, fatty alcohol ether sulfates, glycerol ether sulfates, hydroxy mixed ether sulfates, monoglyceride (ether) sulfates, fatty acid amide (ether) sulfates, mono- and dialkyl sulfosuccinates, mono- and dialkyl sulfosuccinamates, sulfo-triglycerides, amide soaps, ether carboxylic acids and salts thereof, fatty acid isethionates, fatty acid sarcosinates, fatty acid taurides, N-acylamino acids, such as, for example, acyl lactylates, acyl tartrates, acyl glutamates and acyl aspartates, alkyl oligo-glucoside sulfates, protein fatty acid condensates (in particular wheat-based vegetable products) and alkyl (ether) phosphates. If the anionic surfactants contain polyglycol ether chains, these may have a conventional homolog distribution, but preferably have a narrowed homolog distribution.

Typical examples of nonionic surfactants are alkylphenol polyglycol ethers, fatty acid polyglycol esters, fatty acid amide polyglycol ethers, fatty amine polyglycol ethers, alkoxylated triglycerides, mixed ethers, hydroxy mixed ethers, unoxidized or partially oxidized alk(en)yl oligoglycosides or glucuronic acid derivatives, fatty acid N-alkylglucamides, protein hydrolysates (in particular wheat-based vegetable products), polyol fatty acid esters, sugar esters, sorbitan esters, polysorbates and amine oxides. If the nonionic surfactants contain polyglycol ether chains, these may have a conventional homolog distribution, but preferably have a narrowed homolog distribution.

Typical examples of cationic surfactants are quaternary ammonium compounds such as, for example, dimethyl distearyl ammonium chloride, and ester quats, in particular quaternized fatty acid trialkanolamine ester salts. Typical examples of amphoteric or zwittionic surfactants are alkylbetaines, alkylamidobetaines, aminopropionates, aminoglycinates, imidazoliniumbetaines and sulfobetaines. Said surfactants are exclusively known compounds. With regard to structure and preparation of these substances, reference may be made to relevant review works, for example J. Falbe (ed.), "Surfactants in Consumer Products", Springer Verlag, Berlin, 1987, pp. 54–124 or J. Falbe (ed.), "Katalysatoren, Tenside und Mineralöladditive", Thieme Verlag, Stuttgart, 1978, pp. 123–217.

Typical examples of particularly suitable surfactants are fatty alcohol polyglycol ether sulfates, monoglyceride sulfates, mono- and/or dialkyl sulfosuccinates, fatty acid isethionates, fatty acid sarcosinates, fatty acid taurides, fatty acid glutamates, α-olefinsulfonates, ether carboxylic acids, fatty acid glucamides, alkylamidobetaines, amphoacetals and/or protein fatty acid condensates, the latter preferably based on wheat proteins.

Alkyl and/or Alkenyl Oligoglycosides

Performance investigations demonstrate that mixtures of mixed ethers and alkyl and/or alkenyl oligoglycosides are particularly advantageous. The latter are known nonionic surfactants which conform to the formula (II),

in which $R^2$ is an alkyl and/or alkenyl radical having 4 to 22 carbon atoms, G is a sugar radical having 5 or 6 carbon atoms and p is a number from 1 to 10. They can be obtained by the relevant processes of preparative organic chemistry. By way of representation for the extensive literature, reference may be made here to the specifications EP-A1 0301298 and WO 90/03977.

The alkyl and/or alkenyl oligoglycosides can be derived from aldoses or ketoses having 5 or 6 carbon atoms, preferably from glucose. The preferred alkyl and/or alkenyl oligoglycosides are thus alkyl and/or alkenyl oligoglucosides. The index number p in the general formula (II) gives the degree of oligomerization (DP), i.e. the distribution of mono- and oligoglycosides, and is a number between 1 and 10. While p in a given compound must always be an integer and can here primarily assume the values p=1 to 6, the value p for a certain alkyl oligoglycoside is an analytically determined calculated parameter which in most cases is a fraction. Preference is given to using alkyl and/or alkenyl oligoglycosides with an average degree of oligomerization p of from 1.1 to 3.0. From a performance viewpoint, preference is given to those alkyl and/or alkenyl oligoglycosides whose degree of oligomerization is less than 1.7 and is in particular between 1.2 and 1.4.

The alkyl or alkenyl radical $R^2$ can be derived from primary alcohols having 4 to 11, preferably 8 to 10, carbon atoms. Typical examples are butanol, caproic alcohol, caprylic alcohol, capric alcohol and undecyl alcohol, and technical-grade mixtures thereof, as are obtained, for example, in the hydrogenation of technical-grade fatty acid methyl esters or in the course of the hydrogenation of aldehydes from the Roelen oxo synthesis. Preference is given to alkyl oligoglucosides of chain length $C_8$–$C_{10}$ (DP=1 to 3) which are produced as for runnings during the distillative separation of technical-grade $C_8$–$C_{18}$-coconut fatty alcohol and may be contaminated with a content of less than 6% by weight of $C_{12}$-alcohol, and also alkyl oligoglucosides based on technical-grade $C_{9/11}$-oxo alcohols (DP=1 to 3). The alkyl or alkenyl radical $R^2$ can also be derived from primary alcohols having 12 to 22, preferably 12 to 14, carbon atoms. Typical examples are lauryl alcohol, myristyl alcohol, cetyl alcohol, palmoleyl alcohol, stearyl alcohol, isostearyl alcohol, oleyl alcohol, elaidyl alcohol, petroselinyl alcohol, arachyl alcohol, gadoleyl alcohol, behenyl alcohol, erucyl alcohol, brassidyl alcohol, and technical-grade mixtures thereof, which can be obtained as described above. Preference is given to alkyl oligoglucosides based on hydrogenated $C_{12/14}$-coconut alcohol with a DP of from 1 to 3. The alkyl and/or alkenyl oligoglycosides can, based on the wet wipes, be used in amounts of 0.05 to 2% by weight and preferably 0.5 to 1% by weight and, based on the concentrates, in amounts of from 10 to 50% by weight, preferably 25 to 25% by weight, where the weight ratio of mixed ethers to glycoside may be in the range from 10:90 to 90:10, preferably 25:75 to 75:25 and in particular 40:60 to 60:40.

Tissue Papers and Tissue Fabrics for Moistened Papers

Tissue papers to which the present invention refers can be single-ply or multi-ply. The papers generally have a weight per square meter of from 10 to 65 g, preferably 15 to 30 g, and a density of 0.6 g/cm³ and below. Examples of tissue papers to which the invention may extend are, in addition to household wipes, naturally also toilet papers, pocket tissues, face-cleansing wipes, make-up removal wipes, refreshing wipes and the like. In addition to the paper-based tissues, corresponding tissue fabrics which are prepared from fiber or fleece material are also suitable.

Industrial Applicability

Finally, the invention provides for the use of linear and/or branched alcohol polyglycol ethers as impregnating agents for the production of wet wipes, in which they can be used in amounts of from 0.01 to 2% by weight, preferably 0.5 to 1% by weight, based on the wipes.

Auxiliaries and Additives

In a further embodiment of the invention, the wet wipes can comprise further customary auxiliaries and additives, in particular complexing agents, such as, for example, citric acid, HEDP or EDTA, which serve both for the stabilization of the ingredients and also for improving the cleaning performance in the case of salt-containing soilings (e.g. water hardness), antibacterial active ingredients such as, for example, hydrogen peroxide and cationic surfactants, preferably ester quats, and skin care agents. Suitable skin care agents are primarily refatting agents, oil components and emulsifiers, as are typically used in cosmetic products.

Oily Bodies

Suitable oily bodies are, for example, Guerbet alcohols based on fatty alcohols having 6 to 18, preferably 8 to 10, carbon atoms, esters of linear $C_6$–$C_{22}$-fatty acids with linear or branched $C_6$–$C_{22}$-fatty alcohols or esters of branched $C_6$–$C_{13}$-carboxylic acids with linear or branched $C_6$–$C_{22}$-fatty alcohols, such as, for example, myristyl myristate, mynstyl palmitate, myristyl stearate, myristyl isostearate. myristyl oleate, mynstyl behenate, myristyl erucate, cetyl myristate, cetyl palmitate, cetyl stearate, cetyl isostearate, cetyl oleate, cetyl behenate, cetyl erucate, stearyl myristate, stearyl palmitate, stearyl stearate, stearyl isostearate, stearyl oleate, stearyl behenate, stearyl erucate, isostearyl myristate, isostearyl palmitate, isostearyl stearate, isostearyl isostearate, isostearyl oleate, isostearyl behenate, isostearyl oleate, oleyl myristate, oleyl palmitate, oleyl stearate, oleyl isostearate, oleyl oleate, oleyl behenate, oleyl erucate, behenyl myristate, behenyl palmitate, behenyl stearate, behenyl isostearate, behenyl oleate, behenyl behenate, behenyl erucate, erucyl myristate, erucyl palmitate, erucyl stearate, erucyl isostearate, erucyl oleate, erucyl behenate and erucyl erucate. Also suitable are esters of linear $C_6$–$C_{22}$-fatty acids with branched alcohols, in particular 2-ethylhexanol, esters of $C_{18}$–$C_{38}$-alkylhydroxycarboxylic acids with linear or branched $C_6$–$C_{22}$-fatty alcohols (cf. DE 19756377 A1), in particular dioctyl malate, esters of linear and/or branched fatty acids with polyhydric alcohols (such as, for example, propylene glycol, dimerdiol or trimertriol) and/or Guerbet alcohols, triglycerides based on $C_6$–$C_{10}$-fatty acids, liquid mono-/di-/triglyceride mixtures based on $C_6$–$C_{18}$-fatty acids, esters of $C_6$–$C_{22}$-fatty alcohols and/or Guerbet alcohols with aromatic carboxylic acids, in particular benzoic acid, esters of $C_2$–$C_{12}$-dicarboxylic acids with linear or branched alcohols having 1 to 22 carbon atoms or polyols having 2 to 10 carbon atoms and 2 to 6 hydroxyl groups, vegetable oils, branched primary alcohols, substituted cyclohexanes, linear and branched $C_6$–$C_{22}$-fatty alcohol carbonates such as, for example, dicaprylyl carbonate (Cetiol® CC), Guerbet carbonates based on fatty alcohols having 6 to 18, preferably 8 to 10, carbon atoms, esters of benzoic acid with linear and/or branched $C_8$–$C_{22}$-alcohols (e.g. Finsolv® TN), linear or branched, symmetrical or asymmetrical dialkyl ethers having 6 to 22 carbon atoms per alkyl group, such as, for example, dicaprylyl ether (Cetiol® QE), ring-opening products of epoxidized fatty acid esters with polyols, silicone oils (cyclomethicones, silicon methicone grades, etc.) and/or aliphatic or naphthenic hydrocarbons such as, for example, squalane, squalene or dialkylcyclohexanes.

Emulsifiers

Suitable emulsifiers are, for example, nonionogenic surfactants from at least one of the following groups:

- addition products of from 2 to 30 mol of ethylene oxide and/or 0 to 5 mol of propylene oxide onto onto fatty acids having 12 to 22 carbon atoms, onto alkyl phenols having 8 to 15 carbon atoms in the alkyl group, and alkylamines having 8 to 22 carbon atoms in the alkyl radical;
- addition products of from 1 to 15 mol of ethylene oxide onto castor oil and/or hydrogenated castor oil;
- addition products of from 15 to 60 mol of ethylene oxide onto castor oil and/or hydrogenated castor oil;
- partial esters of glycerol and/or sorbitan with unsaturated, linear or saturated, branched fatty acids having 12 to 22 carbon atoms and/or hydoxycarboxylic acids having 3 to 18 carbon atoms, and adducts thereof with 1 to 30 mol of ethylene oxide;
- partial esters of polyglycerol (average degree of self-condensation 2 to 8), polyethylene glycol (molecular weight 400 to 5000), trimethylolpropane, pentaerythritol, sugar alcohols (e.g. sorbitol), alkyl glucosides (e.g. methyl glucoside, butyl glucoside, lauryl glucoside), and polyglucosides (e.g. cellulose) with saturated and/or unsaturated, linear or branched fatty acids having 12 to 22 carbon atoms and/or hydroxycarboxylic acids having 3 to 18 carbon atoms, and adducts thereof with 1 to 30 mol of ethylene oxide;
- mixed esters of pentaerythritol, fatty acids, citric acid and fatty alcohol as in German Patent 1165574 and/or mixed esters of fatty acids having 6 to 22 carbon atoms, methyl glucose and polyols, preferably glycerol or polyglycerol.
- mono-, di- and trialkyl phosphates, and also mono-, di- and/or tri-PEG alkyl phosphates and salts thereof;
- wool wax alcohols;
- polysiloxane-polyalkyl-polyether copolymers and corresponding derivatives;
- block copolymers, e.g. polyethylene glycol-30 dipolyhydroxystearate;
- polymer emulsifiers, e.g. Pemulen grades (TR-1, TR-2) from Goodrich;
- polyalkylene glycols and
- glycerol carbonate.

The addition products of ethylene oxide and/or propylene oxide onto fatty acids, alkyl phenols or onto castor oil are known, commercially available products. These are homolog mixtures whose average degree of alkoxylation corresponds to the ratio of the quantitative amounts of ethylene oxide and/or propylene oxide and substrate with which the addition reaction is carried out. $C_{12/18}$-fatty acid mono- and diesters of addition products of ethylene oxide onto glycerol are known from German Patent DE 2024051 as refatting agents for cosmetic preparations.

Typical examples of suitable partial glycerides are hydroxystearic acid monoglyceride, hydroxystearic acid diglyceride, isostearic acid monoglyceride, isostearic acid diglyceride, oleic acid monoglyceride, oleic acid diglyceride, ricinoleic acid monoglyceride, ricinoleic acid diglyceride, linoleic acid monoglyceride, linoleic acid diglyceride, linolenic acid monoglyceride, linolenic acid diglyceride, erucic acid monoglyceride, erucic acid diglycende, tartaric acid monoglyceride, tartaric acid diglyceride, citric acid monoglyceride, citric acid diglycende, malic acid monoglyceride, malic acid diglyceride and technical-grade mixtures thereof which may also contain small amounts of triglyceride as byproducts from the preparation process. Likewise suitable are addition products of from 1 to 30 mol, preferably 5 to 10 mol, of ethylene oxide onto said partial glycerides.

Suitable sorbitan esters are sorbitan monoisostearate, sorbitan sesquilsostearate, sorbitan disostearate, sorbitan triisostearate, sorbitan monooleate, sorbitan sesquioleate, sorbitan dioleate, sorbitan trioleate, sorbitan monoerucate, sorbitan sesquierucate, sorbitan dierucate, sorbitan trierucate, sorbitan monoricinoleate, sorbitan sesquiricinoleate, sorbitan diricinoleate, sorbitan triricinoleate, sorbitan monohydroxystearate, sorbitan sesquihydroxystearate, sorbitan dihydroxystearate, sorbitantiihydroxy-stearate, sorbitan monotartrate, sorbitan sesquitartrate, sorbitan ditartrate, sorbitantritartrate, sorbitan monocitrate, sorbitan sesquicitrate, sorbitan dicitrate, sorbitan tricitrate, sorbitan monomaleate, sorbitan sesquimaleate, sorbitan dimaleate, sorbitan trimaleate and technical-grade mixtures thereof. Also suitable are addition products of from 1 to 30 mol, preferably 5 to 10 mol, of ethylene oxide onto said sorbitan esters.

Typical examples of suitable polyglyceryl esters are polyglyceryl-2 dipolyhydroxystearate (Dehymuls® PGPH), polyglycerol-3 diisostearate (Lameform® TGI), polyglyceryl-4 isostearate (Isolan® GI 34), polyglyceryl-3 oleate, diisostearoyl polyglyceryl-3 diisostearate (Isolan® PDI), polyglyceryl-3 methylglucose distearate (Tego Care® 450), polyglyceryl-3 beeswax (Cera Bellina®), polyglyceryl-4 caprate (polyglycerol caprate T2010/90), polyglyceryl-3 cetyl ether (Chimexane® NL), polyglyceryl-3 distearate (Cremophor® GS 32) and polyglyceryl polyricinoleate (Admul® WOL 1403) polyglyceryl dimerate isoteararate, and mixtures thereof. Examples of further suitable polyol esters are the mono-, di- and triesters of trimethylolpropane or pentaerythritol with lauric acid, coconut fatty acid, tallow fatty acid, palmitic acid, stearic acid, oleic acid, behenic acid and the like, which are optionally reacted with 1 to 30 mol of ethylene oxide.

Zwitterionic surfactants can also be used as emulsifiers. Zwittionic surfactants is the term used to describe those surface-active compounds which contain at least one quaternary ammonium group and at least one carboxylate and one sulfonate group in the molecule. Particularly suitable zwitterionic surfactants are the so-called betaines, such as the N-alkyl-N,N-dimethylammonium glycinates, for example cocoalkyldimethylammonium glycinate, N-acylaminopropyl-N,N-dimethylammonium glycinates, for example cocoacylaminopropyldimethylammonium glycinate, and 2-alkyl-3-carboxymethyl-3-hydroxyethylimidazoline having in each case 8 to 18 carbon atoms in the alkyl or acyl group, and cocoacylaminoethyl hydroxyethylcarboxy-methylglycinate. Particular preference is given to the fatty acid amide derivative known under the CTFA name Cocamidopropyl Betaine. Likewise suitable emulsifiers are ampholytic surfactants. Ampholytic surfactants are to be understood as meaning those surface-active compounds which, apart from a $C_{8/18}$-alkyl- or -acyl group, contain at least one free amino group and at least one —COOH or —SO$_3$H group in the molecule and are capable of forming internal salts. Examples of suitable ampholytic surfactants are N-alkylglycines, N-alkylpropionic acids, N-alkylaminobutyric acids, N-alkylaminodipropionic acids, N-hydroxyethyl-N-alkylamidopropylglycines, N-alkyltaurines, N-alkylsarcosines, 2-alkylaminopropionic acids and alkylaminoacetic acids having in each case about 8 to 18 carbon atoms in the alkyl group. Particularly preferred ampholytic surfactants are N-cocoalkylaminopropionate, cocoacyl-aminoethylaminopropionate and $C_{12/18}$-acylsarcosine. Finally, suitable emulsifiers are also cationic surfactants which are particularly preferably those of the ester quat type, preferably methyl-quaternized difatty acid triethanolamine ester salts.

These preparations are preferably emulsions, preferably microemulsions or PIT emulsions.

EXAMPLES

Examples 1 to 4, Comparative Example C1

Various impregnation solutions were prepared by simply mixing the components; the foaming ability of the mixtures was then determined under dynamic conditions in accordance with the free-falling circulatory method (1% by weight of washing-active substance, 25° C., delivery rate 1 1/min). To test the cleaning performance and the shine retention, the preparations were applied to an absorbent carrier (absorbent tissue paper, three-ply, weight 18 g/m$^2$, 95% by weight of recycled paper content). To determine the cleaning ability on hard and elastic surfaces, a white soil carrier treated with test soiling was wiped with the impregnated wipes under defined conditions. The cleaning effect was measured photoelectrically against the untreated soil carrier (standard=100%). To check shine retention, a high-gloss black tile was cleaned with the impregnated wipes and the difference was determined using a glossimeter (untreated standard=100%). Finally, the wetting power by immersion was measured in accordance with DIN EN 1772 (0.1% by weight of active substance, 20° C.). The composition of the mixtures and the performance results are summarized in Table 1. Examples 1 to 4 are in accordance with the invention, Example C1 serves as a comparison.

Examples 5 and 6, Comparative Example C2

Various impregnation concentrates were prepared and their viscosity (Höppler, 20° C.) and their tendency toward foam formation and their external appearance were investigated. The results are summarized in Table 2. Examples 5 and 6 are in accordance with the invention, Example C2 serves as a comparison.

TABLE 1

Composition of the impregnation solutions and performance results
Quantitative data as % by weight, water ad 100%

|  | 1 | 2 | 3 | 4 | C1 |
|---|---|---|---|---|---|
| Composition |  |  |  |  |  |
| Carrier | 25.0 | 25.0 | 25.0 | 25.0 | 25.0 |
| $C_{12}$–$C_{14}$-cocoalcohol + 5EO + 4PO | 1.0 | 0.2 | 0.2 | — | — |
| Ethylene glycol + 20EO + 40PO | — | — | — | 0.2 | — |
| $C_8$–$C_{10}$-alkyl oligoglucoside | — | 0.8 | — | 0.8 | — |
| $C_8$–$C_{16}$-alkyl oligoglucoside | — | — | 0.8 | — | — |
| Isodecanol + 8EO | — | — | — | — | 1.0 |
| Citric acid | 0.1 | 0.1 | 0.1 | 0.1 | 0.1 |
| Isopropyl alcohol | 5.0 | 5.0 | 5.0 | 5.0 | 5.0 |
| Hydrogen peroxide | 0.8 | 0.8 | 0.8 | 0.8 | 0.8 |
| Performance properties |  |  |  |  |  |
| Foaming ability [ml] | 600 | 700 | 700 | 700 | 900 |
| Cleaning power [% rel.] | 45 | 55 | 50 | 55 | 35 |
| Shine retention [% rel.] | 75 | 95 | 85 | 95 | 70 |
| Wetting power [s] | 40 | 23 | 25 | 23 | 60 |

TABLE 2

Composition of the impregnation solution concentrates and performances results
Quantitative data as % by weight, water ad 100%

|  | 5 | 6 | C2 |
|---|---|---|---|
| Composition |  |  |  |
| $C_{12}$–$C_{14}$-cocoalcohol + 5EO + 4PO | 10.0 | 10.0 | — |
| $C_8$–$C_{10}$-alkyl oligoglucoside | 40.0 | — | — |
| $C_8$–$C_{16}$-alkyl oligoglucoside | — | 40.0 | — |
| Isodecanol + 8 EO | — | — | 50.0 |
| Bronidox[1] | 0.03 | 0.03 | 0.03 |
| Citric acid | 0.1 | 0.1 | 0.1 |
| Performance properties |  |  |  |
| Viscosity [mPas] | 250 | 260 | >3000 |
| Appearance | clear, homogeneous | clear, homogeneous | cloudy |
| Tendency toward foam formation | low | low | high |

[1]Propylene glycol (and) 5-bromo-5-nitro-1,3-dioxane

What is claimed is:

1. A cleansing article comprising a substrate capable of absorbing and retaining a fluid therein, the substrate being impregnated with a cleaning composition comprising a linear and/or branched alcohol polyglycol ether and an alkyl and/or alkenyl oligoglycoside.

2. The article of claim 1 wherein the linear and/or branched alcohol polyglycol ether is present in the composition in an amount of from about 0.05 to 2% by weight, based on the weight of the article.

3. The article of claim 1 wherein the linear and/or branched alcohol polyglycol ether is present in the composition in an amount of from about 0.1 to 0.5% by weight, based on the weight of the article.

4. The article of claim 1 wherein the cleaning composition further comprises a surfactant, other than the linear and/or branched alcohol polyglycol ether and the alkyl and/or alkenyl oligoglycoside, selected from the group consisting of an anionic surfactant, a nonionic surfactant, a cationic surfactant, an amphoteric surfactant, a zwitterionic surfactant, and mixtures thereof.

5. The article of claim 1 wherein the alkyl and/or alkenyl oligoglycoside is present in the composition in an amount of from about 0.05 to 2% by weight, based on the weight of the composition.

6. The article of claim 1 wherein the alkyl and/or alkenyl oligoglycoside is present in the composition in an amount of from about 0.5 to 1% by weight, based on the weight of the composition.

7. A process for cleaning a hard surface comprising contacting the hard surface with a cleansing article comprising a substrate capable of absorbing and retaining a fluid therein, the substrate being impregnated with a cleaning composition comprising a linear and/or branched alcohol polyglycol ether and an alkyl and/or alkenyl oligoglycoside.

8. The process of claim 7 wherein the linear and/or branched alcohol polyglycol ether is present in the composition in an amount of from about 0.05 to 2% by weight, based on the weight of the article.

9. The process of claim 7 wherein the linear and/or branched alcohol polyglycol ether is present in the composition in an amount of from about 0.1 to 0.5% by weight, based on the weight of the article.

10. The process of claim 7 wherein the cleaning composition further comprises a surfactant, other than the linear and/or branched alcohol polyglycol ether and the alkyl and/or alkenyl oligoglycoside, selected from the group consisting of an anionic surfactant, a nonionic surfactant, a cationic surfactant, an amphoteric surfactant, a zwitterionic surfactant, and mixtures thereof.

11. The process of claim 10 wherein the surfactant is an alkyl and/or alkenyl oligoglycoside.

12. The process of claim 11 wherein the alkyl and/or alkenyl oligoglycoside is present in the composition in an amount of from about 0.05 to 2% by weight, based on the weight of the composition.

13. The process of claim 11 wherein the alkyl and/or alkenyl oligoglycoside is present in the composition in an amount of from about 0.5 to 1% by weight, based on the weight of the composition.

* * * * *